United States Patent
Detjen et al.

(10) Patent No.: US 10,604,458 B2
(45) Date of Patent: Mar. 31, 2020

(54) SYSTEMS AND METHODS FOR AROMATIC ALKYLATION

(71) Applicant: ExxonMobil Chemical Patents Inc., Baytown, TX (US)

(72) Inventors: Todd E. Detjen, Houston, TX (US); John S. Kennedy, Houston, TX (US); Catherine M. Dorsi, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/184,248

(22) Filed: Nov. 8, 2018

(65) Prior Publication Data

US 2019/0161420 A1    May 30, 2019

Related U.S. Application Data

(60) Provisional application No. 62/592,720, filed on Nov. 30, 2017.

(51) Int. Cl.
| | |
|---|---|
| C07C 2/00 | (2006.01) |
| C07C 2/86 | (2006.01) |
| B01D 3/14 | (2006.01) |
| B01D 5/00 | (2006.01) |
| B01D 53/14 | (2006.01) |
| C07C 7/00 | (2006.01) |
| B01D 53/00 | (2006.01) |
| C07C 7/09 | (2006.01) |
| C07C 7/04 | (2006.01) |

(52) U.S. Cl.
CPC .............. *C07C 2/864* (2013.01); *B01D 3/141* (2013.01); *B01D 5/003* (2013.01); *B01D 53/002* (2013.01); *B01D 53/1418* (2013.01); *B01D 53/1425* (2013.01); *B01D 53/1487* (2013.01); *C07C 7/005* (2013.01); *C07C 7/04* (2013.01); *C07C 7/09* (2013.01); *B01D 2257/7027* (2013.01)

(58) Field of Classification Search
CPC ......... C07C 15/06; C07C 15/08; C07C 2/864; C07C 7/005; C07C 7/04; C07C 7/09; B01D 2257/7027; B01D 3/141; B01D 53/002; B01D 53/1418; B01D 53/1425; B01D 53/1487; B01D 5/003
See application file for complete search history.

(56) References Cited

U.S. PATENT DOCUMENTS

| | | | |
|---|---|---|---|
| 6,504,072 B1 | 1/2003 | Brown et al. | |
| 6,642,426 B1 | 11/2003 | Johnson et al. | |
| 8,399,727 B2 * | 3/2013 | Lattner | C07C 2/864 585/467 |
| 2007/0197845 A1 | 8/2007 | Beech et al. | |
| 2011/0092756 A1 | 4/2011 | Lattner et al. | |

* cited by examiner

*Primary Examiner* — Sharon Pregler (57) ABSTRACT

Methods and related systems are disclosed for condensing a minor portion of an effluent stream from an alkylation reactor by contacting the effluent stream with a first liquid hydrocarbon quench stream and a second liquid hydrocarbon quench stream. The effluent stream includes catalyst fines from the reactor, and at least a portion of the catalyst fines are carried with the condensed minor portion of the effluent stream.

17 Claims, 2 Drawing Sheets

FIG. 1

FIG. 2

SYSTEMS AND METHODS FOR AROMATIC ALKYLATION

CROSS-REFERENCE OF RELATED APPLICATIONS

This application claims priority to and benefit of U.S. Ser. No. 62/592,720, filed Nov. 30, 2017 and is incorporated by reference in its entirety.

TECHNICAL FIELD

This disclosure relates to a process for producing para-xylene by the selective methylation of benzene and/or toluene.

BACKGROUND

Para-xylene (PX) is an important starting material for manufacturing terephthalic acid, which is itself a valuable intermediate in the production of synthetic polyester fibers, films, and resins. These polyester materials have many practical, well known uses, such as in fabrics, carpets, and apparel.

One known route for the manufacture of PX is by the methylation of benzene and/or toluene. For example, U.S. Pat. No. 6,504,072 discloses a process for the selective production of PX which comprises reacting toluene with methanol under alkylation conditions in the presence of a catalyst comprising a porous crystalline material having a Diffusion Parameter for 2,2 dimethylbutane of about 0.1-15 $sec^{-1}$ when measured at a temperature of 120° C. and a 2,2 dimethylbutane pressure of 60 torr (8 kPa) wherein said porous crystalline material has undergone prior treatment with steam at a temperature of at least 950° C. to adjust the Diffusion Parameter of said material to about 0.1-15 $sec^{-1}$. The reaction can be carried out in a fixed, moving, or fluid catalyst bed.

In addition, U.S. Pat. No. 6,642,426 discloses a process for alkylating an aromatic hydrocarbon reactant, especially toluene, with an alkylating reagent comprising methanol to produce an alkylated aromatic product, comprising: introducing the aromatic hydrocarbon reactant into a reactor system at a first location, wherein the reactor system includes a fluidized bed reaction zone comprising a temperature of 500 to 700° C. and an operating bed density of about 300 to 600 $kg/m^3$, for producing the alkylated aromatic product; introducing a plurality of streams of said alkylating reactant directly into said fluidized bed reaction zone at positions spaced apart in the direction of flow of the aromatic hydrocarbon reactant, at least one of said streams being introduced at a second location downstream from the first location; and recovering the alkylate aromatic product, produced by reaction of the aromatic reactant and the alkylating reagent, from the reactor system.

The reaction of toluene and/or benzene and methanol, particularly using the highly steamed catalyst described in the '072 patent is highly selective to the production of PX. However, in addition to PX the reaction product contains water, as a necessary by-product of the substitution of a hydrogen group of the benzene ring by the methyl group of the methanol. Other side reactions generate small quantities of oxygenated organic species, many of which are organic acids, such as formic acid, acetic acid and alkyl phenols (such as, methyl, dimethyl and ethyl phenols). Thus the effluent from a toluene and/or benzene methylation reaction includes product xylene, unreacted toluene and/or benzene, light gas products, heavier aromatic species and an aqueous vapor phase. Where the reaction is conducted in a fluidized bed, such as disclosed in the '426 patent, the effluent will also contain catalysts fines which are not recovered by the catalyst separation system of the reactor. These catalysts fines mostly end up in the aqueous phase which, by virtue of the presence of the organic acids, has a low pH. Such an environment is conducive to partial dissolution of the catalyst fines rendering them "sticky" and difficult to separate from the water/oil mixture. This solids separation problem is accentuated by the fact that the solids are in low concentration requiring the processing of large volumes of liquid in the solids recovery step (such as, filtration).

There is therefore a need for an effective process for recovering catalyst fines from the reaction effluent of a fluid bed methylation process that avoids the processing of a low pH aqueous phase having a very dilute catalyst solids concentration.

BRIEF SUMMARY

Some embodiments disclosed herein are directed to a process including (a) reacting an aromatic feedstock comprising benzene with methanol under alkylation conditions in a reactor in the presence of a fluidized bed of solid catalyst particles to produce a vapor phase effluent comprising toluene, xylenes, water, unreacted benzene and solid catalyst fines. In addition, the process includes (b) contacting the vapor phase effluent with a first liquid phase hydrocarbon quench stream to produce a mixture having a higher dew point than the vapor phase effluent. Further, the process includes (c) contacting the mixture with a second liquid phase hydrocarbon quench stream after (b) under conditions to condense a minor portion of the mixture and produce a condensate which contains at least some of the catalyst fines and which is substantially free of an aqueous phase. Still further, the process includes (d) separating at least a portion of the condensate containing said fines from the remainder of the mixture.

Other embodiments are directed to a process including (a) reacting an aromatic feedstock comprising benzene with methanol under alkylation conditions in a reactor in the presence of a fluidized bed of solid catalyst particles to produce a vapor phase effluent comprising toluene, xylenes, water, unreacted benzene and solid catalyst fines. In addition, the process includes (b) flowing the vapor phase effluent to a quench vessel, (c) flowing a first liquid phase hydrocarbon quench stream to the quench vessel, and (d) flowing a second liquid phase hydrocarbon quench stream to the quench vessel independently of the first liquid phase hydrocarbon quench stream. Further, the process includes (e) contacting the vapor phase effluent with each of the first liquid phase quench stream and the second liquid phase hydrocarbon quench stream in the quench vessel under conditions to condense a minor portion of the vapor phase effluent and produce a condensate which contains at least some of the catalyst fines and which is substantially free of an aqueous phase. Still further, the process includes (f) separating at least a portion of the condensate containing said fines from the remainder of the vapor phase effluent.

Still other embodiments are directed to a system including a reactor and a quench vessel. The reactor is coupled to the quench vessel such that an effluent containing catalyst fines emitted from the reactor is flowed to the quench vessel. The quench vessel is configured to condense a minor portion of the effluent from the reactor and produce a condensate which contains at least some of the catalyst fines and which is substantially free of an aqueous phase. In addition, the system includes a product recovery section. The product recovery section is configured to receive a portion of a condensate. Further, the system includes a first recycle line coupling the product recovery section to the quench vessel. The product recovery section is configured to emit a first liquid hydrocarbon quench stream and direct the first liquid hydrocarbon quench stream to the quench vessel via the recycle line. Still further, the system includes a second recycle line extending from a first position on the quench vessel to a second position on the quench vessel. The first position is lower than the second position, and the second recycle line is configured to circulate a second liquid hydrocarbon quench stream within the quench vessel. The first recycle line and the second recycle line are configured such that the first liquid hydrocarbon quench stream and the second liquid hydrocarbon quench stream are provided independently to the quench vessel.

DETAILED DESCRIPTION

The following discussion is directed to various embodiments. However, it should be appreciated that the embodiments disclosed herein have broad application, and that the discussion of any embodiment is meant only to be exemplary of that embodiment, and not intended to suggest that the scope of the disclosure, including the claims, is limited to that embodiment. In the drawings, certain features and components herein may be shown exaggerated in scale or in somewhat schematic form and some details of conventional elements may not be shown in interest of clarity and conciseness. All documents described herein are incorporated by reference, including any priority documents and/or testing procedures, to the extent they are not inconsistent with this text. When numerical lower limits and numerical upper limits are listed herein, ranges from any lower limit to any upper limit are contemplated.

As used herein, the term "catalyst fines" means the small particles of catalytic material, generally having an average diameter of less than 20 microns, that are produced as a result of continued impact between the catalyst particles in the fluidized bed of catalyst employed in the present process.

As used herein the term "fluidized bed" means a zone or vessel wherein particulates contact with gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below about 95%. Description of the minimum fluidization velocity is given in, for example, Chapter 3 of "Fluidization Engineering," D. Kunii and O. Levenspiel, $2^{nd}$ Edition, Butterworth-Heinemami, Boston, 1991 and Chapter 6 of "Chemical Process Equipment," S. M. Walas, Butterworth-Heinemann, Boston, 1990, the entirety of which are incorporated by reference.

This disclosure relates to a process for producing PX by reacting an aromatic feedstock comprising toluene and/or benzene with methanol under alkylation conditions in the presence of a fluidized bed of solid catalyst particles. The process produces a vapor phase effluent comprising the desired PX, water, unreacted benzene, toluene, and solid catalyst fines. To assist in separating the catalyst fines from the vapor phase effluent, the effluent is contacted with one or more liquid hydrocarbon quench streams so as to condense a minor portion of the vapor phase effluent and produce a condensate which contains at least some of the catalyst fines and which is substantially free of an aqueous phase. In particular, in at least some embodiments, the vapor phase effluent is contacted with both a first liquid hydrocarbon quench stream to increase the dew point of the mixture of the vapor phase effluent and a second liquid hydrocarbon quench stream to produce the condensate previously described above, respectively. After separating the resulting condensate from the remainder of the vapor phase effluent, the catalyst fines are generally removed, possibly for recycling to the alkylation step, and, after cooling, the condensate can be recycled to the quench step (e.g., as one of the liquid hydrocarbon quench streams).

Alkylation Process

The alkylation process employed herein can utilize any aromatic feedstock comprising toluene and/or benzene, although in general it is preferred that the aromatic feed contains at least some benzene. In at least some embodiments, the aromatic feedstock comprises at least 90 weight %, especially at least 99 weight %, of benzene, toluene or a mixture thereof. An aromatic feed containing at least 99 weight % benzene may be utilized in some embodiments.

Similarly, although the composition of the methanol-containing feed is not critical, it is generally desirable to employ feeds containing at least 90 weight %, especially at least 99 weight %, of methanol.

In at least some embodiments, the catalyst employed in the present process is a porous crystalline material, typically having a Diffusion Parameter for 2,2 dimethylbutane of about 0.1-15 $sec^{-1}$ when measured at a temperature of 120° C. and a 2,2 dimethylbutane pressure of 60 torr (8 kPa).

As used herein, the Diffusion Parameter of a particular porous crystalline material is defined as $D/r^2 \times 10^6$, wherein D is the diffusion coefficient ($cm^2/sec$) and r is the crystal radius (cm). The required diffusion parameters can be derived from sorption measurements provided the assumption is made that the plane sheet model describes the diffusion process. Thus for a given sorbate loading Q, the value $Q/Q_{13}$, where $Q_{13}$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The porous crystalline material is preferably a medium pore size aluminosilicate zeolite. Medium pore zeolites are generally defined as those having a pore size of about 5 to about 7 Angstroms, such that the zeolite freely sorbs molecules such as n-hexane, 3-methylpentane, benzene and PX. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. In addition to the medium pore size aluminosilicate zeolites, other medium pore acidic metallosilicates, such as silicoaluminophosphates (SAPOs), can be used in the present process.

Particular examples of suitable medium pore zeolites include ZSM-5, ZSM-11, ZSM-12, ZSM-22, ZSM-23, ZSM-35, and ZSM-48, with ZSM-5 and ZSM-11 being particularly preferred. In one embodiment, the zeolite employed in the process of the invention is ZSM-5 having a silica to alumina molar ratio of at least 250, as measured prior to any treatment of the zeolite to adjust its diffusivity.

Zeolite ZSM-5 and the conventional preparation thereof are described in U.S. Pat. No. 3,702,886. Zeolite ZSM-11 and the conventional preparation thereof are described in U.S. Pat. No. 3,709,979. Zeolite ZSM-12 and the conventional preparation thereof are described in U.S. Pat. No. 3,832,449. Zeolite ZSM-23 and the conventional preparation thereof are described U.S. Pat. No. 4,076,842. Zeolite ZSM-35 and the conventional preparation thereof are described in U.S. Pat. No. 4,016,245. ZSM-48 and the conventional preparation thereof is taught by U.S. Pat. No. 4,375,573. The entire disclosures of these U.S. patents are incorporated herein by reference.

The medium pore zeolites described above are used in at least some embodiments of the present process since the size and shape of their pores favor the production of PX over the other xylene isomers (i.e., meta-xylene and ortho-xylene). However, conventional forms of these zeolites have Diffusion Parameter values in excess of the 0.1-15 $sec^{-1}$ range desired for the present process. Nevertheless, the required diffusivity can be achieved by severely steaming the zeolite so as to effect a controlled reduction in the micropore volume of the catalyst to not less than 50%, and preferably 50-90%, of that of the unsteamed catalyst. Reduction in micropore volume is derived by measuring the n-hexane adsorption capacity of the zeolite, before and after steaming, at 90° C. and 75 torr n-hexane pressure.

Steaming of the porous crystalline material is effected at a temperature of at least about 900° C., preferably about 950 to about 1075° C., and most preferably about 1000 to about 1050° C. for about 10 minutes to about 10 hours, preferably from 30 minutes to 5 hours.

To effect the desired controlled reduction in diffusivity and micropore volume, it may be desirable to combine the porous crystalline material, prior to steaming, with at least one oxide modifier, preferably selected from oxides of the elements of Groups IIA, IIIA, IIIB, IVA, VA, VB and VIA of the Periodic Table (IUPAC version). Most preferably, said at least one oxide modifier is selected from oxides of boron, magnesium, calcium, lanthanum and most preferably phosphorus. In some cases, it may be desirable to combine the porous crystalline material with more than one oxide modifier, for example a combination of phosphorus with calcium and/or magnesium, since in this way it may be possible to reduce the steaming severity needed to achieve a target diffusivity value. The total amount of oxide modifier present in the catalyst, as measured on an elemental basis, may be between about 0.05 and about 20 wt. %, and preferably is between about 0.1 and about 10 wt. %, based on the weight of the final catalyst.

Where the modifier includes phosphorus, incorporation of modifier in the catalyst described herein is conveniently achieved by the methods described in U.S. Pat. Nos. 4,356,338; 5,110,776; 5,231,064; and 5,348,643, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt. %.

After contacting with the phosphorus-containing compound, the porous crystalline material may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 30 minutes, at least 1 hour, at least 3-5 hours or more.

Representative phosphorus-containing compounds which may be used to incorporate a phosphorus oxide modifier into the catalyst of the invention include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$ and secondary, $R_2P(O)OX$, phosphonic acids, such as benzene phosphonic acid, the corresponding sulfur derivatives such as $RP(S)(SX)_2$ and $R_2P(S)SX$, the esters of the phosphonic acids, such as dialkyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof such as the monopropyl ester, alkyl dialkylphosphinites, $(RO)PR_2$, and dialkyl alkyphosphinite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$, and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphorochloridites, $(RO)PCl$, dialkylphosphinochloroidites, $R_2PCl$, alkyl alkylphosphonochloridates, $(RO)(R)P(O)Cl$, dialkyl phosphinochloridates, $R_2P(O)Cl$, and $RP(O)Cl_2$. Applicable corresponding sulfur derivatives include $(RS)PCl_2$, $(RS)_2PCl$, $(RS)(R)P(S)Cl$, and $R_2P(S)Cl$.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-$P_2O_5$ reaction products.

Representative boron-containing compounds which may be used to incorporate a boron oxide modifier into the catalyst of the invention include boric acid, trimethylborate, boron oxide, boron sulfide, boron hydride, butylboron dimethoxide, butylboric acid, dimethylboric anhydride, hexamethylborazine, phenyl boric acid, triethylborane, diborane and triphenyl boron.

Representative magnesium-containing compounds include magnesium acetate, magnesium nitrate, magnesium benzoate, magnesium propionate, magnesium 2-ethylhexoate, magnesium carbonate, magnesium formate, magnesium oxylate, magnesium bromide, magnesium hydride, magnesium lactate, magnesium laurate, magnesium oleate, magnesium palmitate, magnesium salicylate, magnesium stearate and magnesium sulfide.

Representative calcium-containing compounds include calcium acetate, calcium acetylacetonate, calcium carbonate, calcium chloride, calcium methoxide, calcium naphthenate, calcium nitrate, calcium phosphate, calcium stearate and calcium sulfate.

Representative lanthanum-containing compounds include lanthanum acetate, lanthanum acetylacetonate, lanthanum carbonate, lanthanum chloride, lanthanum hydroxide, lanthanum nitrate, lanthanum phosphate and lanthanum sulfate.

The porous crystalline material employed in the present process may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of porous crystalline material and inorganic oxide matrix vary widely, with the content of the former ranging from about 1 to about 90% by weight and more usually, particularly when the composite is prepared in the form of beads, in the range of about 2 to about 80 wt. % of the composite.

In one embodiment, the binder material comprises silica or a kaolin day. Procedures for preparing silica-bound zeolites, such as ZSM-5, are described in U.S. Pat. Nos. 4,582,815; 5,053,374; and 5,182,242. A particular procedure for binding ZSM-5 with a silica binder involves an extrusion process.

In the present process, the methanol and aromatic feeds are contacted with the catalyst described above with the catalyst particles being disposed in one or more fluidized beds. Each of the methanol and aromatic feeds can be injected into the fluidized catalyst in a single stage. However, in a preferred embodiment, the methanol feed is injected in stages into the fluidized catalyst at one or more locations downstream from the location of the injection of the aromatic reactant into the fluidized catalyst. For example, the aromatic feed can be injected into a lower portion of a single vertical fluidized bed of catalyst, with the methanol being injected into the bed at a plurality of vertically spaced intermediate portions of the bed and the product being removed from the top of the bed. Such a system is generally disclosed in U.S. Pat. No. 9,095,831, the contents of which are incorporated herein by reference in their entirety. Alternatively, the catalyst can be disposed in a plurality of vertically spaced catalyst beds, with the aromatic feed being injected into a lower portion of the first fluidized bed and part of the methanol being injected into an intermediate portion of the first bed and part of the methanol being injected into or between adjacent downstream catalyst beds.

Irrespective of the disposition of the catalyst, as the reaction proceeds the catalyst gradually deactivates as a result of build-up of carbonaceous material, generally referred to as "coke" on the catalyst. Thus, a portion of the catalyst in the/each fluidized bed is generally withdrawn, either on a continuous or a periodic basis, and fed to a separate regenerator. In the regenerator, the catalyst, again in the form of a fluidized bed, is contacted with an oxygen-containing gas, such as air, at a temperature between about 400 and about 700° C. so as to burn off the coke and regenerate the catalyst. The regenerated catalyst is continuously or periodically returned to the alkylation reactor, whereas the exhaust gas from the regenerator is scrubbed to remove entrained catalyst fines. The separated fines can be returned to the regenerator and/or purged to control the build-up of fines in the catalyst inventory.

The conditions employed in the alkylation stage of the present process are not narrowly constrained but, in the case of the methylation of toluene, generally include the following ranges: (a) temperature between about 500 and about 700° C., such as between about 500 and about 600° C.; (b) pressure of between about 1 atmosphere and about 1000 psig (between about 100 and about 7000 kPa), such as between about 10 psig and about 200 psig (between about 170 and about 1480 kPa); (c) moles toluene/moles methanol (in the reactor charge) of at least about 0.2, and preferably from about 0.2 to about 20; and (d) a weight hourly space velocity ("WHSV") for total hydrocarbon feed to the reactor(s) of about 0.2 to about 1000, preferably about 0.5 to about 500 for the aromatic reactant, and about 0.01 to about 100 for the combined methanol reagent stage flows, based on total catalyst in the reactor(s).

Product Treatment and Recovery

The product of the reaction between the methanol and aromatic feeds is a gaseous effluent comprising PX, toluene (e.g., unreacted toluene or toluene resulting from the reaction), water vapor, unreacted benzene, unreacted methanol, light olefins and other light gas by-products, generally some $C_{9+}$ aromatic by-products and entrained solid catalyst and catalyst fines. Thus the gaseous effluent leaving the (final) fluidized bed reactor is generally passed through an integral cyclone separator to remove some of the entrained catalyst solids and return them to the alkylation reactor. However, even after passage through the cyclone separator, the product effluent still inevitably contains some solid catalyst fines and the present process provides a simple and efficient process of removing the catalyst fines from the product effluent and recycling the fines back to the methylation step.

The product effluent leaves the fluidized bed reactor system at a high temperature, typically between about 500 and about 600° C., and initially may be passed through a heat exchanger so that the waste heat in the effluent stream may be recovered and used to heat other process stream(s). It is, however, preferred that any initial cooling of the product stream is limited so as to keep the effluent vapors well above the dew point, typically about 95 to 130° C. Conveniently, the temperature of the effluent after waste heat recovery is between about 150 and about 500° C.

Following initial cooling, the effluent vapor stream is subjected to a quench step in which the effluent is contacted with one or more liquid hydrocarbon quench streams to further cool and partially condense the effluent. In addition, contact of the effluent with at least one of the liquid hydrocarbon quench streams is designed to sufficiently raise a dew point of the mixture of the effluent and the at least one liquid hydrocarbon quench stream above that of water to avoid condensing an aqueous phase from the effluent before a liquid hydrocarbon condensate phase during the quench step. The quantity and temperature of the liquid hydrocarbon quench stream are controlled so that only a minor portion of the effluent stream, typically less than 40 wt. %, such as less than 20 wt. %, for example less than 10 wt. %, less than 5 wt. %, of the effluent stream, is recovered as a liquid product from the quench step. The resulting condensate, made up of the hydrocarbon quench streams plus the condensed effluent including some of the catalyst fines, are separated from the vapor and, by controlling the amount of effluent condensed in the quench step, it is found that the condensate is substantially free of a separate water phase. It is to be understood that the condensate will contain some quantity of dissolved water, but should not contain any (or very little in some embodiments) free water (as evidenced by either a cloudy appearance of the condensate or by the appearance of a phase separation upon standing). This is important since the presence of a separate water phase will make concentration of the solid catalyst fines from the condensate more difficult.

The liquid hydrocarbon(s) used for the quench step should generally contain less than 1 volume % free water and preferably no visible free water. Apart from this the liquid hydrocarbon(s) used for the quench step can be any aliphatic or aromatic hydrocarbon having from 6 to 12 carbon atoms. It is, however, generally preferred to employ hydrocarbons from within the process, particularly some or all of the condensate from the quench step and/or hydrocarbons produced from a downstream separation step. In these cases, the quench oil may or may not contain catalyst fines. In one embodiment, a $C_{7+}$, $C_{8+}$, or $C_{9+}$ hydrocarbon stream produced from a separation unit or apparatus downstream of the alkylation reactor is used as a first quench oil by recycling the separated hydrocarbon stream to the quench step and the condensate (which may contain $C_{6+}$ or $C_{7+}$ aromatic hydrocarbons and small amount of dissolved water) from the quench step itself is used as a second quench oil by recirculating the condensate through a cooler to control the heat removed, without separating the catalyst fines from the condensate. Alternatively, at least a portion of the condensate may undergo processing to remove solid material. This "solids-free" condensate may be used advantageously to "scrub" the vapor from the quench step to further reduce any solids entrainment with the vapor product.

The quench step should be designed to maximize the solids removal efficiency from the effluent vapor and into the condensate. This may be achieved in some embodiments, by using a column with the liquid hydrocarbon quench stream(s) circulating through the column countercurrent to the effluent vapor stream. The column typically contains internals, such as trays or packing, to maximize the contacting area between the vapor and liquid phases. Alternatively, a single stage scrubber may be used, such as a venturi scrubber, to contact the liquid hydrocarbon quench stream with the effluent vapor. This device is typically co-current, with liquid and vapor flowing in the same direction. A high degree of contacting is achieved through intense mixing of fine liquid drops with the vapor stream in a high-velocity zone. With this alternative, a downstream separator is used to separate the vapor from the solids-containing liquid.

The net liquid removed from the quench step contains catalyst fines in a much higher concentration than would be found from cooling of the complete effluent stream approaching ambient conditions. In addition, this concentrated solids-in-oil stream does not contain any free water (or very little free water in some embodiments). The stream may, however, undergo or more processing steps to further concentrate the solids. Various methods are available for this additional solids concentration, including but not limited to filtration, settling, and electrostatic precipitation.

It may be desirable to return the concentrated catalyst fines to the methylation step, in order to reduce catalyst losses and to improve the fluidization properties in the fluid bed reactor. Conveniently, the concentrated catalyst fines are returned to the reactor as a slurry in a liquid flush stream. Typically, the flush stream comprises the aromatic feedstock and/or methanol, such as at least 90 volume % aromatic feedstock plus methanol and less than 5 volume %, such as less than 2 volume %, for examples less than 1 volume %, free water. In one embodiment, the flush stream comprises a sidestream from the detoluenizer column in the downstream separation process.

After subjecting the gaseous reactor effluent to the quench step and separating the condensate thereby generated, the remaining gaseous effluent is typically at a temperature between about 100 and about 150° C. The remaining effluent is then cooled further, typically to a temperature between about 25 and about 70° C., and fed to a three-phase separator where the effluent separates into a liquid organic phase rich in the aromatic components of the effluent, a liquid aqueous phase containing most of unreacted methanol, and a gaseous phase containing most of the light gas by-products. The organic phase is recovered from the separator and passed to a first distillation column (e.g., the detoluenizer column) to remove the benzene and/or toluene (either as unreacted components or reaction products) and then to a second distillation column to remove the $C_{9+}$ aromatic by-products and recover the PX product.

Figure 1:
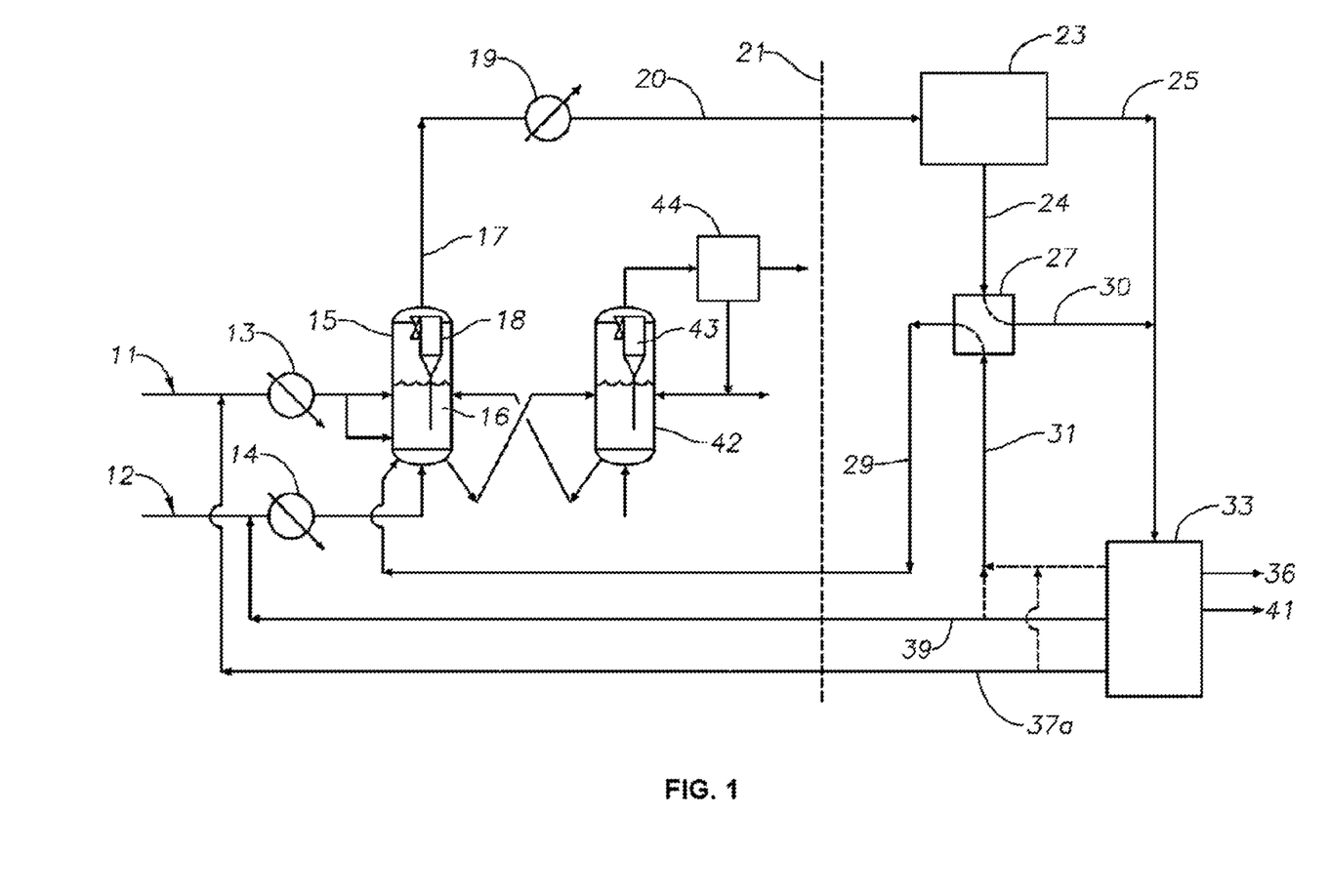
FIG. 1 is a flow diagram of a process for methylating benzene according to at least some embodiments.
Figure 2:
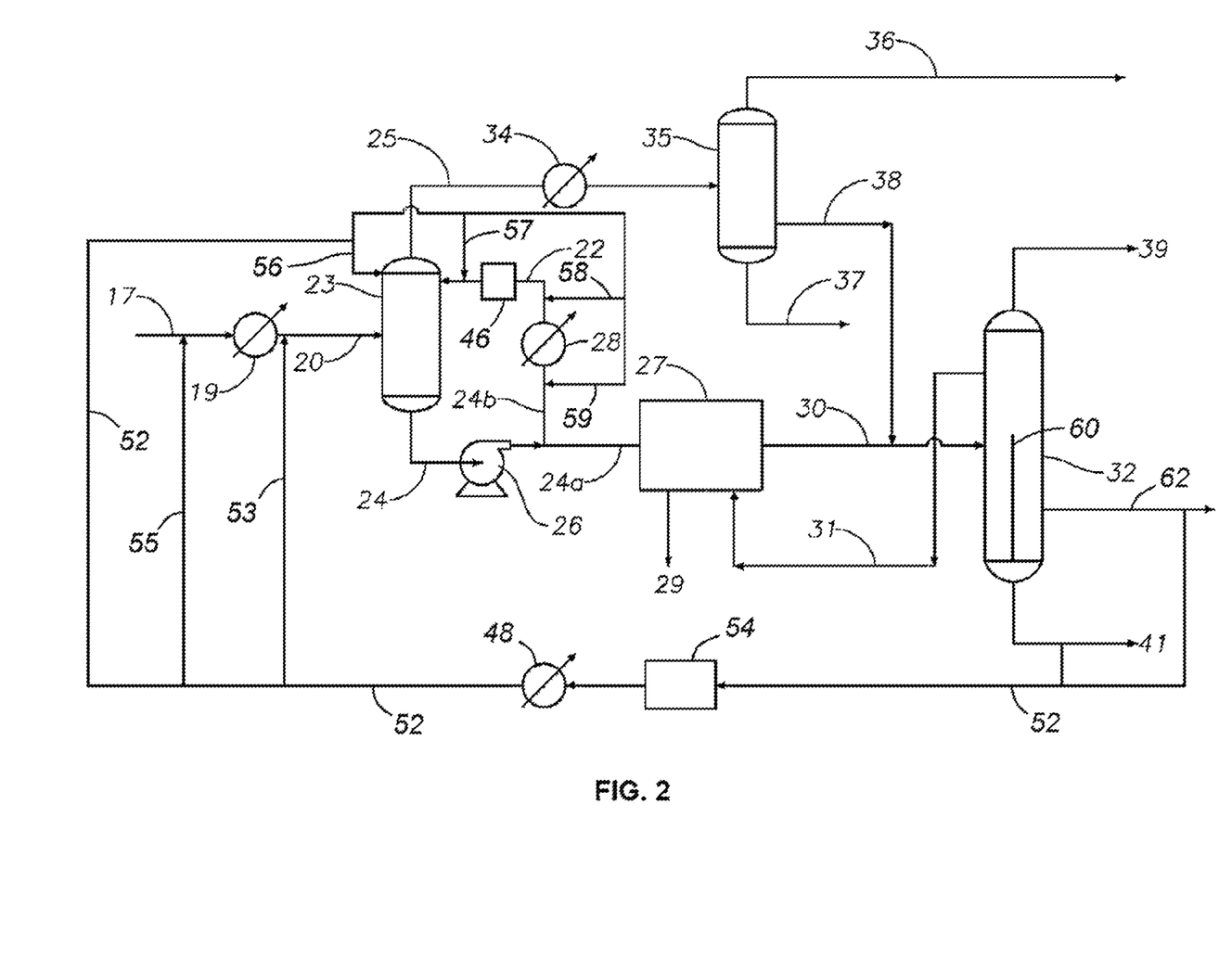
FIG. 2 is a flow diagram of part of the product treatment and recovery stages of the process shown in FIG. 1.

One embodiment of a process for producing PX by the reaction of methanol with a benzene containing stream will now be more particularly described with reference to the accompanying drawings, in which FIG. 1 illustrates the overall process and FIG. 2 illustrates part of product treatment and recovery stages of the process. While the description of the specific embodiment of FIG. 1 and FIG. 2 below discusses a benzene containing stream that is initially fed to the methylation reactor (e.g., reactor 15), it should be appreciated that in various embodiments the aromatic fed to the methylation reactor may comprise, toluene, benzene, or some combination thereof.

Referring initially to FIG. 1, methanol and benzene feeds 11, 12 respectively are passed through heaters 13, 14 respectively and supplied to a vertically disposed reactor 15 containing a fluidized bed of catalyst 16. In this embodiment, the heated benzene feed 12 is supplied to the base of the reactor 15, whereas the heated methanol feed is split and supplied to reactor 15 at a plurality of vertically spaced locations above the base of the reactor 15. The methanol and benzene react in the reactor 15 to produce a gaseous product effluent 17 which contains entrained catalyst solids. The effluent is therefore initially passed through a cyclone separator 18 to remove part of the catalyst solids and return them to the fluidized bed 16. On leaving the reactor 15, the gaseous effluent 17 comprises the desired PX, toluene, water vapor, unreacted benzene and methanol, light gas by-products, $C_{9+}$ aromatic by-products and a small amount, generally less than 0.5 wt. %, of solid catalyst fines which were not removed by the cyclone separator 18.

As shown in FIG. 1, part of the catalyst in the reactor 15 is periodically or continuously regenerated in a regenerator 42 and the exhaust gas from the regenerator is passed through a cyclone separator 43 to remove catalyst fines. The fines are collected in a recovery unit 44, and are optionally recycled to the regenerator 42 and/or purged. By purging the catalyst fines recovered from the regenerator effluent, rather than from the product effluent 17, it is possible to ensure that the purged fines are substantially free, that is contain less than 10 wppm, such as less than 5 wppm, for example less than 1 wppm, of aromatic contamination.

Referring now to FIG. 1 and FIG. 2, the gaseous effluent 17 is initially passed through a heat exchanger 19 where waste heat is recovered and the cooled effluent stream 20 is then passed to a product treatment and recovery section illustrated generally at 21 in FIG. 1 and shown in more detail in FIG. 2. The first stage of product treatment and recovery involves contacting the gaseous effluent with one or more liquid hydrocarbon quench streams (e.g., the streams carried in lines 52, 22) in and proximate to a quench column 23 (e.g., upstream of quench column 23) so as to cool and partially condense the effluent to produce a liquid condensate stream 24 and a gaseous product stream 25.

The liquid condensate stream 24 is substantially free of an aqueous phase and contains most of the catalyst fines entrained in the gaseous effluent 17. A pump 26 removes the liquid condensate stream 24 from the quench column 23 and feeds a first part 24(a) of the stream 24 to a solids concentration unit 27 and a second part 24(b) to a heat exchanger 28 where the second part of the condensate stream is cooled to produce the quench stream 22 (which may be referred to herein as the "second liquid hydrocarbon quench stream"). Thus, second part 24(b) of stream 24 and stream 22 may together be referred to herein as a recycle stream. In some embodiments, quench stream 22 may comprise $C_{6+}$ or $C_{7+}$ aromatics with some dissolved water.

Stream 24(a) is the "net" condensate produced from the quench step. The catalyst fines in the stream 24(a) are concentrated in the unit 27, for example by filtration, electrostatic precipitation, and/or centrifuging. After concentration of fines in unit 27, the "net" condensate stream leaves the unit as stream 30, which is substantially free of catalyst fines. Optionally, the fines concentrated in unit 27 can be removed from the unit 27 as an outlet stream 29 by washing with a toluene flush stream 31. As shown in FIG. 1, the catalyst-containing outlet stream 29 is then recycled to the reactor 15. Alternately, the concentrated catalyst fines can be removed from unit 27 without washing or flushing with a flush stream. After removal of the catalyst fines, stream 30 is fed to a detoluenizer column 32 (see FIG. 2) which forms part of the product recovery section illustrated generally at 33 in FIG. 1.

Referring specifically now to FIG. 2, after leaving the quench column 23, the gaseous product stream 25 is cooled in a heat exchanger 34 and passed to a three-phase separator 35 where the effluent separates into a liquid organic phase rich in the aromatic components of the effluent stream 20, a liquid aqueous phase containing most of unreacted methanol and a gaseous phase containing most of the light gas by-products. The gaseous phase is removed from the separator 35 as an overhead stream 36, which can be treated to separate the light olefins and other useful light gas by-products, whereas the liquid aqueous phase is removed as a recycle steam 37, from which the methanol is recovered and recycled to the reactor 15 (see stream 37a in FIG. 1). The liquid organic phase is removed from the separator 35 as a product steam 38 and is combined with the fines-free first part of the condensate (i.e., stream 30) and fed to the detoluenizer column 32. In this embodiment, the column 32 separates the combined product stream (i.e., the combination of stream 30 and 38) into a toluene-rich overhead stream 39, which is recycled to the reactor 15, and a bottoms stream 41 containing the PX product together with any $C_{9+}$ by-products (and toluene in at least some embodiments). In some embodiments, the bottoms stream 41 is fed to a further distillation unit (not shown) to separate the desired PX product from the heavier aromatic by-products. While detoluenizer column 32 is shown and described as a single distillation column, it should be appreciated that any suitable separation apparatus or unit (or multiple separation apparatus or units) may be used in other embodiments.

In addition, as shown, the heavier aromatic by-products (e.g., such as those contained in stream 41) can optionally be recycled as an additional liquid hydrocarbon quench stream 52 (which may be referred to herein as the "first liquid hydrocarbon quench stream"). As a result, in these embodiments, liquid hydrocarbon quench stream 52 (or more simply "quench stream 52") may be referred to herein as a recycle stream. As illustrated in FIG. 2, quench stream 52 may be combined or mixed with effluent stream 17 either upstream of quench column 23 or within quench column 23 along with quench stream 22. It should be appreciated that various routing options are shown for quench stream 52 in FIG. 2 (e.g., lines 53, 55, 56, 57, 58, 59, etc.). However, not all of the routing options are utilized simultaneously in some embodiments (although use of combinations of these various routing options for quench stream 52 are certainly contemplated). Each of the various routing options for quench stream 52 will be discussed in more detail below.

In particular, in some embodiments, quench stream 52 is combined with effluent stream 17 upstream of quench column 23 via either lines 55 or 53. In some embodiments, it is desirable to independently cool quench stream 52 prior to combination with effluent stream 17. As a result, in these embodiments, quench stream 52 is routed through heat exchanger 48 prior to combination with effluent stream 17 via lines 53 or 55. In these embodiments, heat exchanger 48 may cool quench stream 55 to between 85 and 250° C. In at least some embodiments, heat exchanger 48 may not cool below the dew point of the aqueous phase of effluent stream 17 (e.g., which in some embodiments is approximately 100° C.). In addition to or alternatively to heat exchanger 48, quench stream 52 may be routed through heat exchanger 19 along with effluent stream 17. Choosing to or to not route quench stream 52 through heat exchanger 19 (either in addition to or alternatively to routing stream 52 through heat exchanger 48) will dictate the choice of using lines 55, 53.

Either additionally or alternatively, in some embodiments, quench stream 52 may be mixed with effluent 17 within quench column 23 itself along with quench stream 22. In particular, in some embodiments, quench stream 52 may be sent directly into quench column 23 independently of both effluent stream 17 and quench stream 22 (e.g., via line 56 in FIG. 2). In at least some embodiments, quench stream 52 may be sent to an upper (or uppermost) portion of quench column 22 (however, other injection locations are contemplated).

In some embodiments, quench stream 52 may be mixed with quench stream 22 prior to streams 22, 52 entering quench column 23 and contacting effluent stream 17. For example, in some embodiments, quench stream 52 is merged with quench stream 22 via any one of the lines 57, 58, 59 prior to either stream 22, 52 entering quench column 23. For example, quench stream 52 may be merged or mixed with quench stream 22 either upstream or downstream of heat exchanger 28 via lines 58 and 59, respectively. As previously described above, quench stream 52 may be initially routed through heat exchanger 48 prior to merging streams 52, 22.

Alternatively, quench stream 22 may include a filtration unit 46, which may be similarly configured as filtration unit 27, previously described. Thus, filtration unit 46 may be configured to reduce or remove catalyst fines that may be present within quench stream 22. As shown in FIG. 2, filtration unit 46 may be disposed along stream 22 downstream of heat exchanger 28 and upstream of quench column 23. However, in other embodiments, filtration unit 46 may be disposed upstream of heat exchanger 28 (e.g., between heat exchanger 28 and pump 26 or even upstream of pump 26). In some embodiments, quench stream 52 may be merged or mixed with quench stream 22 either upstream or downstream of filter unit 46 via lines 58 or 57, respectively. As described above for solids concentration unit 27, any catalyst fines removed via filtration unit 46 may be returned to reactor 15 to reduced overall catalyst losses during operations.

In embodiments disclosed herein, quench stream 52 will have a higher dew point than quench stream 22 and has a dew point that is higher than the aqueous phase. As a result, when quench stream 52 is mixed with effluent stream 17, the overall dew point of the mixture is raised, thereby avoiding the initial condensation of the aqueous phase as described herein. In addition, it should be appreciated that in these embodiments, quench stream 52 will include less water than quench stream 22. Finally, in some embodiments where quench stream 52 is contacted with effluent stream 17 within quench tower 23 (e.g., via line 56), quench stream 52 may be contacted concurrently with effluent stream 17, and quench stream 22 may be contacted counter currently with effluent stream 17. In still other embodiments, both quench streams 22, 52 are contacted either concurrently or counter currently with effluent stream 17 within quench tower 23.

Referring still to FIG. 2, quench stream 52 may be filtered prior to mixing with either effluent stream 17 and/or stream 22 or before entering column 23. For example, quench stream 52 may be routed through a filtration unit 54 downstream of detoluenizer column 32. Filtration unit 54 may be similarly configured to filtration units 27 or 46 and thus is configured to remove or at least reduce the amount of catalyst fines within quench stream 52. As discussed above for units 27, 46, any catalyst fines removed via filtration unit 54 may be returned to reactor 15 to reduce overall catalyst losses during operations.

In some embodiments, quench stream 52 is derived from an overhead product stream taken from a downstream distillation column In these embodiments, catalyst fines are recycled to a less volatile stream removed via the bottom of the column In still other embodiments, quench stream 52 may be taken from the bottoms stream of a tower downstream of detoluenizer column 32 (e.g., such as a $C_{9+}$ stream).

In still other embodiments, quench stream 52 may be originated from a divided wall column (e.g., in FIG. 2, detoluenizer 32 is shown as a divided wall column for illustration purposes). In these embodiments, stream 52 may be taken as a side stream (e.g., stream 62) that is disposed on an opposing side of a dividing wall 60 within column 32. Thus, during operations, catalyst fines emitted to column 32 are stopped (at least partially) by the dividing wall 60, and the fluid (with less or no catalyst fines) continues on as quench steam 52.

In a modification of the process shown in FIG. 1 and FIG. 2, the solids concentration unit 27 could be omitted and the first part 24(a) of the condensate stream be fed directly to the detoluenizer column 32. In this option, the solids go to the bottom of the column 32, and eventually leave with the heavy oil byproduct stream 41. At this point, they can either be left in the stream for a fuel application (if solids are within specification limits), or they can be filtered out at that point, where the flow rate is very small.

Referring still to FIG. 1 and FIG. 2, during operations, the flow rates and/or temperatures of both quench streams 22, 52 may be manipulated based on the dew point and/or water content of the effluent stream 17 as well as the dew point of the heavier quench stream 52. In at least some of these embodiments, measurements of the ratio of benzene to toluene in the reactor feed (e.g., stream 12 with or with additional recycle streams), the ratio of toluene to xylene in quench stream 52, the ratio xylene to $C_{9+}$ aromatic hydrocarbons in quench stream 52, and/or the flow rate of methanol to stream 11 may be used to determine the desired flow rates and/or temperatures of quench streams 22, 52. For example, an increase in the ratio of benzene to toluene in the reactor feed stream 12 will result in a decrease in the dew point of both the reactor effluent 17 and the condensed hydrocarbon stream 24b. In these circumstances, the flow rate of the quench stream 52 may be increased to maintain the hydrocarbon dew point inside the quench tower above that of free water.

In addition, in at least some embodiments the flow rates and/or temperatures of quench streams 22, 52 may be adjusted to ensure a proper temperature profile within quench tower 23. For example, if quench stream 52 is cooled prior to introduction into the quench tower 23 (e.g., heat exchanger 48), an increased flow rate of 52 might alter the temperature profile of quench tower 23. In these circumstances, the flow rate of quench stream 52 and/or quench stream 22 may be adjusted to maintain a desired temperature profile within quench tower 23. Further, in at least some embodiments, it may be desirable to maintain a certain flow of quench stream 22 through the filtration unit 46. Thus, in these embodiments the temperature of at least one of the quench streams (e.g., stream 22 or 52) may be adjusted to ensure the proper temperature profile within the quench tower 23.

Without being limited to this or any other theory, when pure or partial benzene streams (e.g., stream 12) are subjected to an alkylation reaction with methanol (e.g., such as in reactor 15) the resulting effluent 17 includes a larger amount of lighter hydrocarbons (e.g., $C_{7-}$ aromatics) as compared with effluent produced from pure toluene alkylation with methanol. This alteration in the character of the effluent 17 results in a lower dew point for effluent 17 that is equal to or below the dew point of water. In addition, in these cases, the quench stream 22, which is derived from the condensed effluent 17 itself, will also include a higher percentage of lighter components (e.g., benzene), so that contacting effluent 17 with quench stream 22 alone will result in the separation of an aqueous phase before adequately removing the catalyst fines via a condensed hydrocarbon phase as previously described above. As a result, the effectiveness of the quench step in these circumstances is frustrated.

However, according to the embodiments disclosed herein, if an additional or alternative quench stream (e.g., quench stream 52) is derived from a concentration of heavier components (e.g., $C_{7+}$, $C_{8+}$, $C_{9+}$ aromatic hydrocarbons) from a downstream separation unit or apparatus (e.g., detoluenizer column 32), contact of this heavier quench stream 52 upstream of or within quench column 23 can effectively raise the relative dew point of the fluid within column 23 above that of water so that a condensed hydrocarbon phase can be separated prior to any aqueous phase and catalyst fines may be separated with this condensate as previously described above. Thus, when a pure or partial benzene stream is subjected to alkylation with methanol in a fluidized bed reactor (e.g., as in reactor 15), use of a heavier quench stream from a downstream separation unit (e.g., detoluenizer column 32) may improve and enhance separation of catalyst fines from the alkylation effluent stream (e.g., effluent stream 17).

In the embodiments disclosed above, quench stream 52 was described as originating from a downstream separation unit/apparatus (e.g., detoluenization column 32). However, it should be appreciated that in other embodiments quench stream 52 may be derived from any suitable source. For example, in some embodiments, quench stream 52 is derived from a reformate fractionation process (e.g., such as those used in chemical plant or refinery processes). In other embodiments, quench stream 52 is derived from a recycle stream of heavy aromatics from a transalkylation process and/or xylene isomerization process. In still other embodiments, quench stream 52 may be derived from a filtrate stream emitted from an aromatic crystallization or adsorptive separation process. In still further embodiments, quench stream 52 may be imported from an exterior location. It should be appreciated that in some embodiments, quench stream 52 may be derived from a combination of the options disclosed herein. Finally, while embodiments have disclosed an alkylation system and process for ultimately producing PX, it should be appreciated that the principles disclosed in the embodiments disclosed herein may be applied to other chemistries, systems, and processes that do not include the production of PX as a primary focus.

While various embodiments have been disclosed herein, modifications thereof can be made without departing from the scope or teachings herein. In particular, many variations and modifications of the systems, apparatus, and processes described herein are possible and are within the scope of the disclosed subject matter. Accordingly, embodiments disclosed herein are exemplary only and are not limiting. As a result, the scope of protection is not limited to the embodiments described herein, but is only limited by the claims that follow, the scope of which shall include all equivalents of the subject matter of the claims. Unless expressly stated otherwise, the steps in a method claim may be performed in any order. The use of identifiers such as (a), (b), (c) before steps in a method claim is not intended to and does not specify a particular order to the steps. Rather the use of such identifiers are used to simplify subsequent reference to such steps. Finally, the use of the term "including" in both the description and the claims is used in an open ended fashion, and should be interpreted as meaning "including, but not limited to."

The invention claimed is:

1. A process, comprising:
    (a) reacting an aromatic feedstock comprising benzene with methanol under alkylation conditions in a reactor in the presence of a fluidized bed of solid catalyst particles to produce a vapor phase effluent comprising toluene, xylenes, water, unreacted benzene and solid catalyst fines;
    (b) contacting the vapor phase effluent with a first liquid phase hydrocarbon quench stream to produce a mixture having a higher dew point than the vapor phase effluent;
    (c) contacting the mixture with a second liquid phase hydrocarbon quench stream after (b) under conditions to condense a minor portion of the mixture and produce a condensate which contains at least some of the catalyst fines and which is substantially free of an aqueous phase; and
    (d) separating at least a portion of the condensate containing said fines from the remainder of the mixture.

2. The process of claim 1, further comprising:
    (e) flowing the condensate to a separation unit;
    (f) separating the first liquid phase hydrocarbon quench stream from the condensate in the separation unit; and
    (g) recycling the first liquid phase hydrocarbon quench stream to the contacting in (b).

3. The process of claim 2, wherein the separation unit is a divided wall column including a divided wall, and wherein the first liquid phase hydrocarbon phase quench stream is emitted from the separation divided wall column on an opposing side of the dividing wall from where the condensate flows into the divided wall column at (g).

4. The process of claim 1, wherein the contacting in (c) occurs within a quench vessel.

5. The process of claim 4, wherein the contacting in (b) occurs upstream of the quench vessel.

6. The process of claim 5, further comprising cooling the vapor phase effluent stream before the contacting in (b).

7. The process of claim 5, further comprising cooling the mixture before the contacting (c).

8. The process of claim 1, wherein the mixture is contacted counter currently with the second liquid phase hydrocarbon quench stream.

9. A process, comprising:
    (a) reacting an aromatic feedstock comprising benzene with methanol under alkylation conditions in a reactor in the presence of a fluidized bed of solid catalyst particles to produce a vapor phase effluent comprising toluene, xylenes, water, unreacted benzene and solid catalyst fines;
    (b) flowing the vapor phase effluent to a quench vessel;
    (c) flowing a first liquid phase hydrocarbon quench stream to the quench vessel;
    (d) flowing a second liquid phase hydrocarbon quench stream to the quench vessel independently of the first liquid phase hydrocarbon quench stream;
    (e) contacting the vapor phase effluent with each of the first liquid phase quench stream and the second liquid phase hydrocarbon quench stream in the quench vessel under conditions to condense a minor portion of the vapor phase effluent and produce a condensate which contains at least some of the catalyst fines and which is substantially free of an aqueous phase; and (f) separating at least a portion of the condensate containing said fines from the remainder of the vapor phase effluent.

10. The process of claim 9, further comprising:

(g) flowing the condensate to a separation unit;

(h) separating the first liquid phase hydrocarbon quench stream from the condensate in the separation unit; and (i) recycling the first liquid phase hydrocarbon quench stream to the contacting in (e).

11. The process of claim 10, wherein the separation unit is a divided wall column including a divided wall, and wherein the first liquid phase hydrocarbon phase quench stream is emitted from the separation divided wall column on an opposing side of the dividing wall from where the condensate flows into the divided wall column at (g).

12. The process of claim 10, further comprising:

(j) cooling at least a portion of the condensate containing the catalyst fines; and (k) recycling the cooled condensate to the contacting in (e) as the second liquid phase hydrocarbon quench stream.

13. The process of claim 12 further comprising:

(l) removing at least a portion of the catalyst fines from the condensate before the recycling in (k).

14. The process of claim 10, wherein the vapor phase effluent has a dew point and wherein the contacting the vapor phase effluent with the first liquid phase quench stream comprises forming a mixture having a dew point that is higher than the dew point of the vapor phase effluent.

15. The process of claim 9, wherein, within the quench vessel, the first liquid phase hydrocarbon quench stream is contacted concurrently with the vapor phase effluent and the second liquid phase hydrocarbon quench stream is contacted counter currently with the vapor phase effluent.

16. The process of claim 9, wherein, within the quench vessel, each of the first liquid phase hydrocarbon quench stream and the second liquid phase hydrocarbon quench stream are contacted concurrently with the vapor phase effluent.

17. The process of claim 9, wherein, within the quench vessel, each of the first liquid phase hydrocarbon quench stream and the second liquid phase hydrocarbon quench stream are contacted counter currently with the vapor phase effluent.

* * * * *